US011399743B2

(12) United States Patent
Lenigk et al.

(10) Patent No.: US 11,399,743 B2
(45) Date of Patent: Aug. 2, 2022

(54) WEARABLE SWEAT SENSING SYSTEMS AND METHODS THEREOF

(71) Applicant: General Electric Company, Schenectady, NY (US)

(72) Inventors: Ralf Lenigk, Niskayuna, NY (US); Azar Alizadeh, Wilton, NY (US); Matthew Jeremiah Misner, New Braunfels, TX (US); Andrew Arthur Paul Burns, Niskayuna, NY (US); Richard Jeanluc St. Pierre, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 567 days.

(21) Appl. No.: 16/442,842

(22) Filed: Jun. 17, 2019

(65) Prior Publication Data

US 2020/0107758 A1 Apr. 9, 2020

Related U.S. Application Data

(60) Provisional application No. 62/743,537, filed on Oct. 9, 2018.

(51) Int. Cl.
*A61B 5/145* (2006.01)
*A61B 5/1477* (2006.01)
(Continued)

(52) U.S. Cl.
CPC ........ *A61B 5/14517* (2013.01); *A61B 5/1477* (2013.01); *A61B 5/4266* (2013.01);
(Continued)

(58) Field of Classification Search
CPC ........... A61B 5/145; A61B 10/00; A61B 5/00; A61B 5/1477; A61B 5/14517;
(Continued)

(56) References Cited

U.S. PATENT DOCUMENTS

| 6,558,320 B1 | 5/2003 | Causey, III et al. |
| 7,383,072 B2 | 6/2008 | Edmonson et al. |

(Continued)

FOREIGN PATENT DOCUMENTS

| WO | 2010045247 A1 | 4/2010 |
| WO | 2017019573 A1 | 2/2017 |

(Continued)

OTHER PUBLICATIONS

Alizadeh, et al. "A wearable patch for continuous monitoring of sweat electrolytes during exertion," Lab Chip, 2018, 18, 2632 (Year: 2018).*

(Continued)

*Primary Examiner* — Eric J Messersmith
(74) *Attorney, Agent, or Firm* — Armstrong Teasdale LLP

(57) ABSTRACT

The systems and methods described herein provide a wearable sweat sensing device. The device includes a sweat patch component including a sweat biochemical sensor patch having a substrate defining a hole, at least one biochemical sensor, and a capture wick including a tip that extends through the hole, the capture wick configured to channel sweat across the at least one biochemical sensor. The sweat patch component further includes a wick downstream from the capture wick and separated from the capture wick by a gap, and electronic circuitry disposed against at least one face of the wick, wherein an electronic response of the electronic circuitry changes as sweat flows through the wick. The wearable sweat sensing device further includes an electronics module component configured to facilitate assessing hydration of a wearer based on signals from the at least one biochemical sensor and the electronic circuitry.

20 Claims, 8 Drawing Sheets

(51) Int. Cl.
*A61B 5/00* (2006.01)
*A61B 10/00* (2006.01)

(52) U.S. Cl.
CPC .......... *A61B 5/4875* (2013.01); *A61B 5/6833* (2013.01); *A61B 10/0064* (2013.01)

(58) Field of Classification Search
CPC ... A61B 5/6833; A61B 5/4266; A61B 5/0537; A61B 5/14546; A61B 5/002; A61B 5/4875; A61B 10/0064; A61B 5/7225; A61B 2560/0214; A61B 2560/0406
See application file for complete search history.

(56) References Cited

U.S. PATENT DOCUMENTS

| | | | |
|---|---|---|---|
| 9,579,040 | B2 | 2/2017 | Rafferty et al. |
| 9,750,429 | B1 | 9/2017 | Sackner et al. |
| 9,867,539 | B2 | 1/2018 | Heikenfeld et al. |
| 10,136,831 | B2 | 11/2018 | Heikenfeld |
| 10,201,279 | B2 | 2/2019 | Heikenfeld et al. |
| 2010/0063372 | A1 | 3/2010 | Potts et al. |
| 2015/0112165 | A1 | 4/2015 | Heikenfeld |
| 2015/0289820 | A1 | 10/2015 | Miller et al. |
| 2016/0213315 | A1 | 7/2016 | Hyde et al. |
| 2017/0054599 | A1 | 2/2017 | Burns et al. |
| 2017/0238854 | A1 | 8/2017 | Henshaw |
| 2017/0296114 | A1 | 10/2017 | Ghaffari et al. |
| 2018/0020966 | A1 | 1/2018 | Begtrup et al. |
| 2018/0153451 | A1 | 6/2018 | Heikenfeld et al. |
| 2018/0153452 | A1 | 6/2018 | Nyberg et al. |
| 2018/0256137 | A1* | 9/2018 | Heikenfeld .......... A61B 5/1477 |
| 2018/0263539 | A1* | 9/2018 | Javey ................. A61B 5/14539 |
| 2018/0289296 | A1* | 10/2018 | Heikenfeld ............ G01N 33/66 |
| 2019/0008448 | A1* | 1/2019 | Begtrup ........... G01N 33/48792 |
| 2019/0231236 | A1* | 8/2019 | Heikenfeld ........ A61B 5/14532 |
| 2019/0307374 | A1* | 10/2019 | Heikenfeld .......... A61B 5/4266 |
| 2020/0155047 | A1* | 5/2020 | Rogers ............... A61B 5/14539 |
| 2020/0298231 | A1* | 9/2020 | Francis ............. B01L 3/502715 |

FOREIGN PATENT DOCUMENTS

| | | |
|---|---|---|
| WO | 2017058806 A1 | 4/2017 |
| WO | 2017070641 A1 | 4/2017 |
| WO | 2018005438 A1 | 1/2018 |
| WO | 2018067412 A1 | 4/2018 |
| WO | 2018071895 A1 | 4/2018 |
| WO | 2018112198 A1 | 6/2018 |

OTHER PUBLICATIONS

Glennon, et al. "DSWEATCHI: A Wearable Platform for Harvesting and Analysing Sweat Sodium Content," Electroanalysis, 2016, 28, 1283-1289 (Year: 2016).*

International Search Report and Written Opinion, dated May 12, 2020, for International application No. PCT/US2019/055213 (12 pgs.).

Liu et al., "A wearable conductivity sensor for wireless real-time sweat monitoring", Sensors and Actuators B: Chemical, vol. 227, pp. 35-42, May 2016.

Koh et al., "A soft, wearable microfluidic device for the capture, storage, and colorimetric sensing of sweat", Science translational medicine, vol. 8, Issue: 366, pp. 35-42, Nov. 23, 2016.

Anastasova et al., "Awearable multisensing patch for continuous sweat monitoring", Biosensors and Bioelectronics, vol. 93, pp. 139-145, Jul. 15, 2017.

Martin et al., "Epidermal Microfluidic Electrochemical Detection System: Enhanced Sweat Sampling and Metabolite Detection", Nov. 2017.

Choi et al., "Skin-interfaced systems for sweat collection and analytics", Applied Sciences and Engineering, vol. 4, Issue: 2, Feb. 16, 2018.

Yin et al., "A Wearable Microfluidic Sensing Patch for Dynamic Sweat Secretion Analysis", ACS Sensors, vol. 03, pp. 944-952, May 9, 2018.

* cited by examiner

WEARABLE SWEAT SENSING SYSTEMS AND METHODS THEREOF

CROSS REFERENCE TO RELATED APPLICATIONS

This application is a non-provisional application and claims priority to U.S. Provisional Patent Application Ser. No. 62/743,537 filed Oct. 9, 2018 for "WEARABLE SWEAT SENSING SYSTEMS", which is hereby incorporated by reference in its entirety.

STATEMENT REGARDING FEDERALLY SPONSORED RESEARCH AND DEVELOPMENT

This invention was made with Government support under contract number FA8650-15-2-5401 awarded by the U.S. Air Force Research Laboratory. The Government has certain rights in this invention.

BACKGROUND

The subject matter described herein relates generally to wearable sensing systems and, more particularly, to wearable systems for sensing sweating of a user.

In circumstances where significant exertion is required by an individual, continuous monitoring of hydration and heat stress of the individual is important, in addition to monitoring other physiological parameters such as heart rate, heart rate variability, motion, temperature, blood oxygenation, etc. Poor management of hydration (including both dehydration and hyperhydration) may result in short-term or long-term injury to the individual. Further, increasing levels of dehydration have been shown to cause impairments during exercise. For example, when levels of dehydration approach approximately 3-4% of body mass loss for an individual, up to a 10% performance decline may result. Dehydration may also adversely affect cognitive function and mood.

Fluid osmolality and fluid volume should be considered when assessing hydration. For example, at least some standard for hydration assessment are based on total body water and plasma osmolality under controlled conditions of stable and equilibrated body fluids. In practice, nude body loss masses may be used as a direct measure of fluid content, but continuous assessment of an individual's nude body mass fluctuations in the field is unrealistic. Similarly, blood (or urine) osmolality measurements are generally intrusive, requiring sophisticated equipment and training for analysis.

BRIEF DESCRIPTION

In one aspect, a wearable sweat sensing device is provided. The device includes a sweat patch component including a sweat biochemical sensor patch having a substrate defining a hole therethrough, at least one biochemical sensor printed on the substrate, and a capture wick extending across the at least one biochemical sensor and including a tip that extends through the hole defined through the substrate to reach the skin of a wearer, the capture wick configured to channel sweat from the skin of the wearer across the at least one biochemical sensor. The sweat patch component further includes a wick downstream from the capture wick and separated from the capture wick by a gap, the wick configured to channel sweat received via the capture wick, and electronic circuitry disposed against at least one face of the wick, wherein an electronic response of the electronic circuitry changes as sweat flows through the wick. The wearable sweat sensing device further includes an electronics module component communicatively coupled to the sweat patch component, the electronics module component configured to facilitate assessing hydration of a wearer based on signals from the at least one biochemical sensor and the electronic circuitry.

In another aspect, a method of assessing hydration of a subject is provided. The method includes adhering a sweat patch component to the subject, the sweat patch component including a capture wick that extends across at least one biochemical sensor, a wick downstream from the capture wick and separated from the capture wick by a gap, and electronic circuitry disposed against at least one face of the wick, receiving signals from the at least one biochemical sensor and the electronic circuitry as sweat is channeled through the capture wick and the wick, wherein an electronic response of the electronic circuitry changes as sweat flows through the wick, and assessing hydration of the subject based on the signals received from the at least one biochemical sensor and the electronic circuitry.

In yet another aspect, a sweat patch component for a wearable sweat sensing device is provided. The sweat patch component includes a sweat biochemical sensor patch including a substrate defining a hole therethrough, at least one biochemical sensor printed on the substrate, and a capture wick extending across the at least one biochemical sensor and including a tip that extends through the hole defined through the substrate to reach the skin of a wearer, the capture wick configured to channel sweat from the skin of the wearer across the at least one biochemical sensor. The sweat patch component further includes a wick downstream from the capture wick and separated from the capture wick by a gap, the wick configured to channel sweat received via the capture wick, and electronic circuitry disposed against at least one face of the wick, the electronic circuitry including first and second conductive traces, and a plurality of water-soluble resistors extending between the first and second conductive traces.

DRAWINGS

These and other features, aspects, and advantages of the present disclosure will become better understood when the following detailed description is read with reference to the accompanying drawings in which like characters represent like parts throughout the drawings, wherein.

Figure 1:
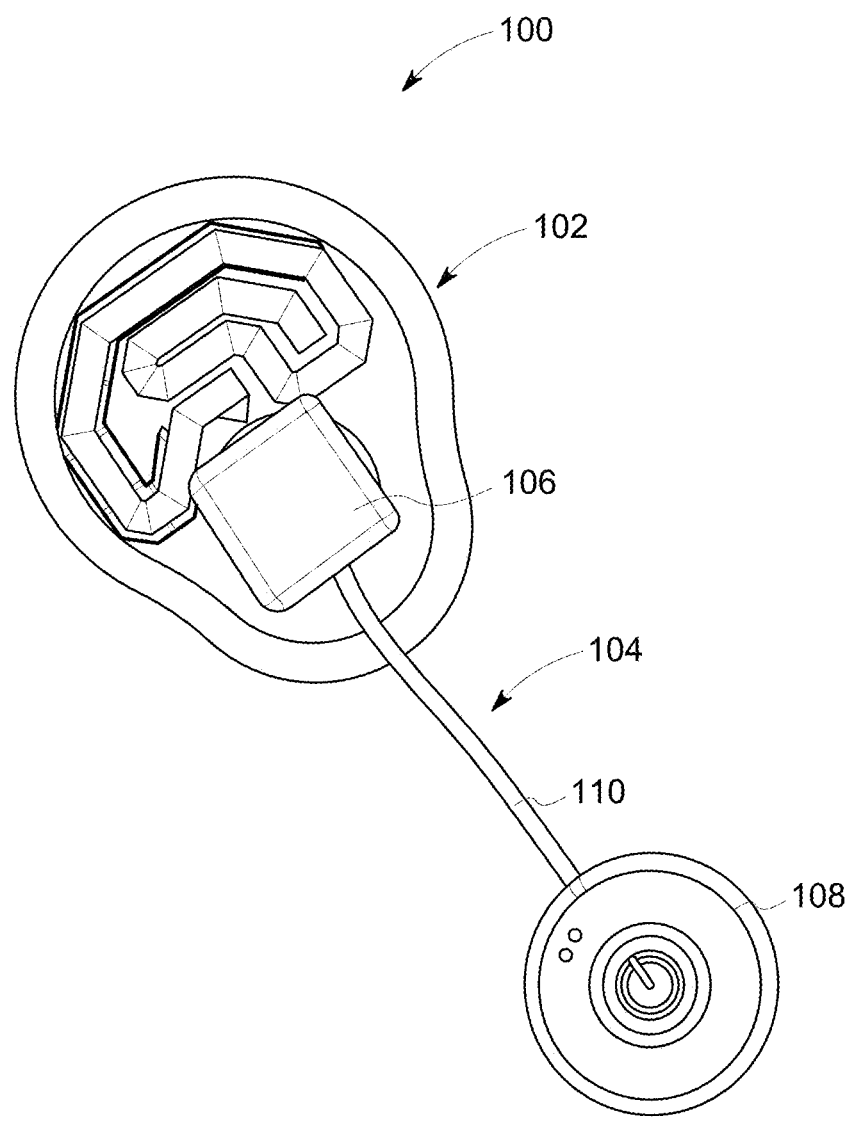
FIG. 1 is a top view of an exemplary wearable sweat sensing device.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about," "substantially," and "approximately," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The systems and methods described herein provide a wearable sweat sensing device. The device includes a sweat patch component including a sweat biochemical sensor patch having a substrate defining a hole therethrough, at least one biochemical sensor printed on the substrate, and a capture wick extending across the at least one biochemical sensor. The capture wick includes a tip that extends through the hole defined through the substrate to reach the skin of a wearer, and the capture wick is configured to channel sweat from the skin of the wearer across the at least one biochemical sensor. The sweat patch component further includes a wick downstream from the capture wick and separated from the capture wick by a gap. The wick is configured to channel sweat received via the capture wick. Further, electronic circuitry is disposed against at least one face of the wick, and an electronic response of the electronic circuitry changes as sweat flows through the wick. An electronics module component is communicatively coupled to the sweat patch component, and is configured to facilitate assessing hydration of a wearer based on signals from the at least one biochemical sensor and the electronic circuitry.

The wearable sweat sensing device described herein allows for non-invasive and real-time hydration measurements. More specifically, the device is capable of measuring changes in overall fluid volume using an in-situ sweat rate sensor. Further, the device is capable of measuring changes in fluid osmolality using multiple sweat biochemical sensors. These measurements can be wirelessly transmitted from the device to a mobile computing device (e.g., a smartphone) using a specialized electronics module containing a multiplexer to facilitate data transmissions from multiple sensors (e.g., via Bluetooth). Further, by using a variable data rate, and controlling which sensors are activated at a given time, the device has an extended battery lifetime, allowing for a smaller form factor (as battery size generally dictates form factor). The device also employs analytics for combining osmolality and fluid volume in a single index.

Body fluid volume (also referred to as fluid balance) may be estimated using the following Equation 1:

$$\text{Fluid balance (mL)} = (\text{dietary fluid intake} + \text{metabolic water production}) - (\text{sweat volume} + \text{urine volume} + \text{transcutaneous water loss} + \text{respiratory water loss}) \quad \text{(Equation 1)}$$

In many scenarios, Equation 1 can be simplified by assuming the metabolic water production is equal to the transcutaneous water loss and the respiratory water loss, resulting in the following Equation 2:

$$\text{Fluid balance (mL)} = \text{dietary fluid intake} - (\text{sweat volume} + \text{urine volume}) \quad \text{(Equation 2)}$$

Further, in scenarios where no water intake or urination occurs during exercise, this can be simplified to the following Equation 3:

$$\text{Fluid balance (mL)} = -\text{sweat volume} \quad \text{(Equation 3)}$$

The wearable sweat sensing device described herein is capable of measuring sweat volume changes over specific period of time (i.e., sweat rate), as described herein. Because the device is placed on a specific body location (e.g., the lower back, the upper arm, etc.), the measured sweat rate is a local sweat rate. Sweat rates at different body locations may differ from each other. Accordingly, to obtain an overall sweat rate for the user's body, appropriate conversion factors are applied to the measured local sweat rate in the exemplary embodiment. During high exertion activities (e.g., military and athletic training), it is important to be able to measure sweat rates continuously. Specifically, sweat is a thermoregulation process, and there is often a strong correlation between changes in core body temperature and body fluid losses (i.e., sweat volume) during intense exertion.

Further, during intense exertion, a user may suffer from different types of dehydration, including isotonic (i.e., equal salt and water loss), hypotonic (i.e., greater salt loss than water loss), and hypertonic (i.e., smaller salt loss than water loss) dehydration. It is important to understand the particular type of dehydration to generate an appropriate fluid and electrolyte replacement plan. Accordingly, the wearable sweat sensing device described herein is capable of acquiring simultaneous, real-time measurements of at least two electrolytes (e.g., sodium and potassium) in some embodiments. Simultaneous measurement of multiple electrolytes is important for a more accurate correlation with plasma. Further, of the solutes in sweat, sodium is generally the most abundant and studied.

Within sweat glands, the sweat sodium concentration is nearly isotonic to the plasma sodium concentration (independent of sweat rate). However, as the sweat moves towards the skin surface, the sweat sodium concentration becomes hypotonic (relative to the plasma sodium concentration) due to sodium adsorption within sweat ducts. This re-adsorption is limited by the rate and capacity limits of sweat ducts to re-adsorb sodium, and thus, the sweat sodium concentration at the skin surface increases with sweat rate. For example, the sweat sodium concentration may range from approximately 20 millimolar (mM) at low sweat rates to approximately 100 mM at high sweat rates. Although there is still some disagreement as to whether a linear relationship between sweat sodium concentration exists, it is generally accepted that within certain sweat rate ranges, a linear relationship exists.

In contrast, sweat potassium and urea concentrations, although not as extensively studied as sweat sodium, appear to be generally independent of sweat rate, likely due to the lack of re-adsorption mechanisms in the sweat ducts. Because potassium concentration in measured sweat is expected to mirror plasma potassium concentration and remain consistent despite changes in sweat rate, sweat potassium concentration may be used as a quality control check.

In some embodiments, the wearable sweat sensing device described herein may be combined with outer sensors, such as skin and core body temperature sensors, heart rate sensors, and/or electrical impedance spectroscopy/tomography sensors for a more holistic assessment of hydration.

The embodiments described herein are not limited to being worn by a human user. For example, the sweat sensing device described herein may be worn by other mammals (e.g., dogs) for sweat monitoring purposes.

Figure 2:
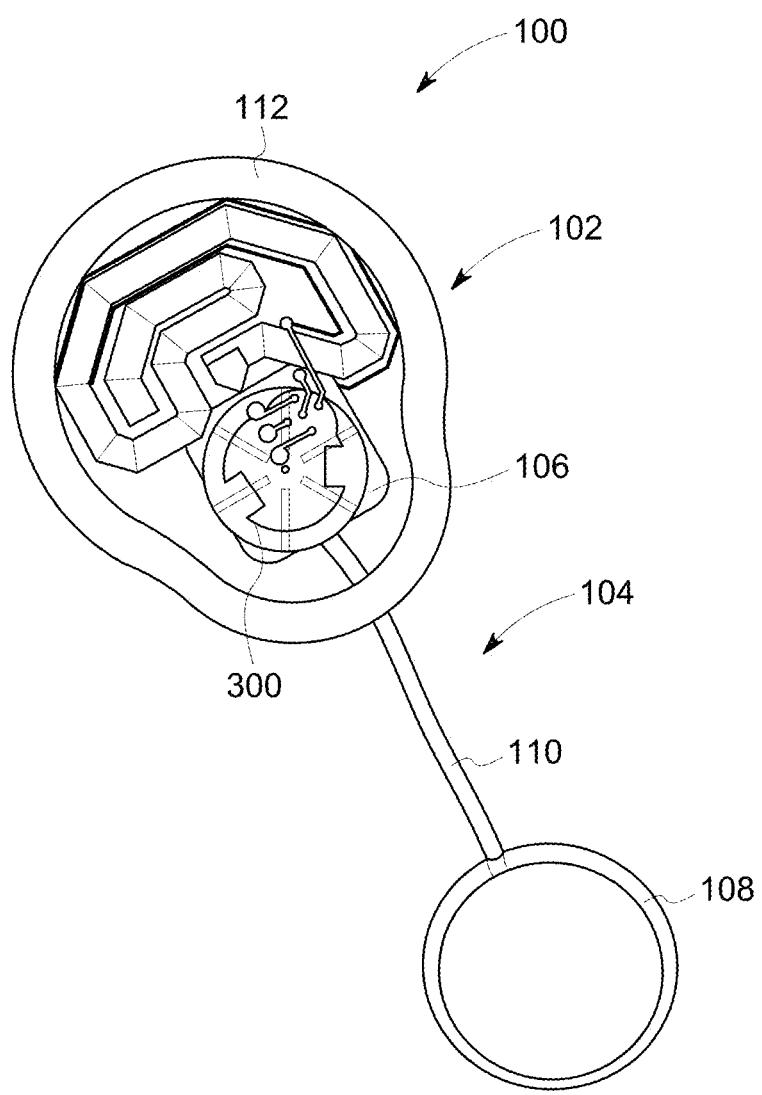
FIG. 2 is a bottom view of the wearable sweat sensing device shown in FIG. 1.

Referring now to the figures, FIG. 1 is a top view of an exemplary embodiment of a wearable sweat sensing device 100, and FIG. 2 is a bottom view of wearable sweat sensing device 100. That is, FIG. 2 shows a side of wearable sweat sensing device 100 that generally contacts a user's skin. As shown in FIGS. 1 and 2, wearable sweat sensing device 100 includes a sweat patch component 102 and an electronics module component 104. Sweat patch component 102 includes biochemical and sweat flow rate sensors, as well as microfluidics for sweat collection and transport, as described in detail below. Electronics module component 104 includes an electronic readout, and communication and energy management components, as described herein. In the exemplary embodiment, sweat patch component 102 is disposable (i.e., sweat patch component 102 is generally used once), and electronics module component 104 is reusable (i.e., electronics module component may be used with multiple sweat patch components 102 for multiple uses).

Electronics module component 104 includes an on-patch electronics module 106, a control module 108, and a cable 110 communicatively coupling on-patch electronics module 106 to control module 108 in the exemplary embodiment. On-patch electronics module 106 may also be referred to herein as an analog-to-digital signal module. Control module 108 may include data storage, power management, and communications components, as described herein. The distributed configuration of electronics module component 104 enables reducing the footprint and weight of the portion of electronics module component 104 in direct contact with the skin (i.e., on-patch electronics module 106). Specifically, on-patch electronics module 106 may be relatively lightweight and have a thin form factors, increasing user comfort and improving robustness of attaching sweat patch component 102 to the user and of wearable sweat sensing device 100 itself. Further, because on-patch electronics module 106 is separate from control module 108, control module 108 may be positioned remotely from sweat patch component 102. Alternatively, on-patch electronics module 106 and control module 108 are incorporated in the same component, and are not located remotely from one another. As another alternative, in some embodiments, on-patch electronics module 106 and control module 108 are located remotely from one another, but are not communicatively coupled using cable 110. Instead, in such embodiments, on-patch electronics module 106 and control module 108 communicate with each other wirelessly, using any suitable wireless communications protocol.

As shown in FIGS. 1 and 2, in the exemplary embodiment, sweat patch component 102 is attached to a user's skin using an adhesive surface 112 or foam. Alternatively, in some embodiments, sweat patch component 102 may be integrated into clothing and held in place using a suction device or compression clothing. Sweat patch component 102 may be affixed to various portions of a user's body, including, but not limited to, the torso, legs, back, neck, arms, etc. For example, sweat patch component 102 may be placed on the lower back (e.g., above the waistline, below the rib cage, and adjacent to the spine on either side), on the upper back (e.g., above or on the scapula), on the chest (e.g., below the pectoral muscle or centrally over the sternum), on the lower leg (e.g., over the gastrocnemius or on the lateral face over the tibialis anterior muscle), or on the upper leg (e.g., on the inner thigh).

Control module 108 may be positioned remotely from any of these locations using cable 110. For example, control module 108 may be stored in a pocket of a garment (e.g., pants or shirt), or may be attached, for example, a belt or a heart-rate monitor strap (e.g., using a clip or hook and loop fasteners). In embodiments where wearable sweat sensing device 100 is incorporated into a garment (e.g., an elastic and form-fitting garment), cable 110 may be a flexible conductor sewn or otherwise incorporated into the garment to allow sweat patch component 102 to be affixed to a particular location, while control module 108 is located in an unobtrusive location (e.g., on the back of a collar or on a sleeve of a shirt, over the sternum, on the hem of pants, in a waistband, in a pocket, etc.) or distributed over other portions of the garment.

Figure 3:
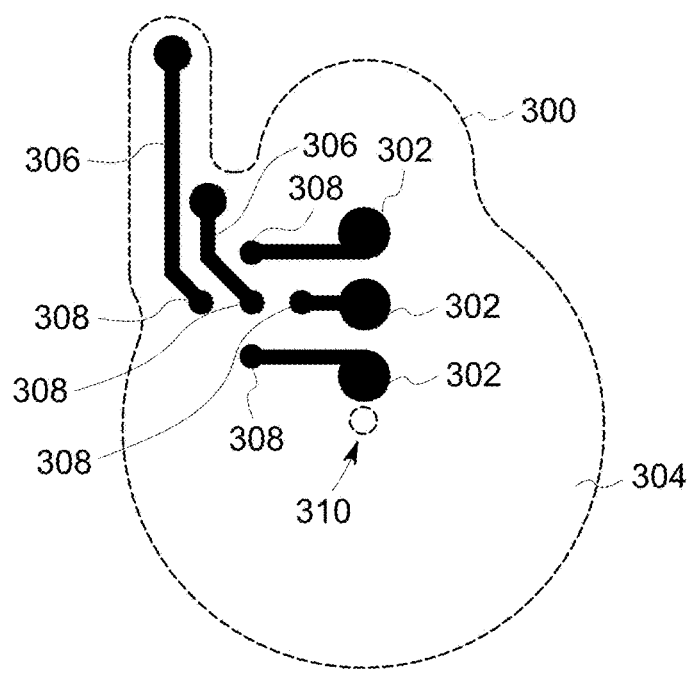
FIG. 3 is a schematic view of an exemplary sweat biochemical sensor patch that may be used with the wearable sweat sensing device shown in FIGS. 1 and 2.
Figure 4:
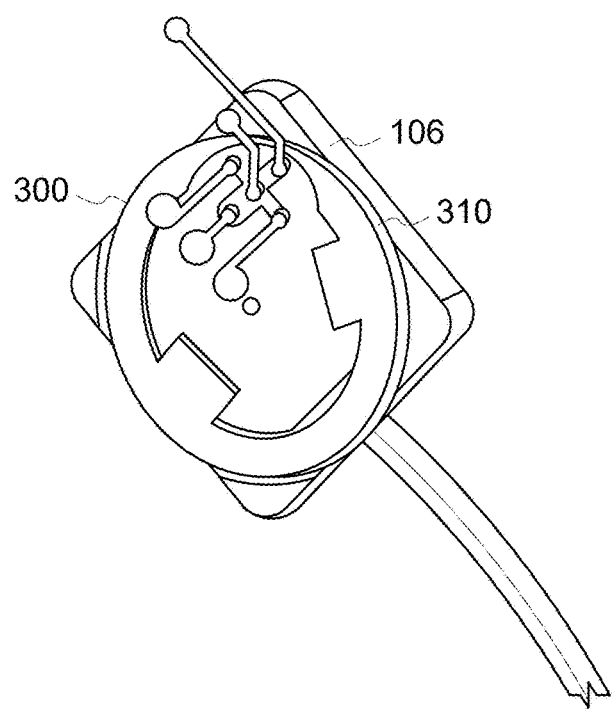
FIG. 4 is a perspective view of the sweat biochemical sensor patch shown in FIG. 3 attached to an on-patch electronics module.

As shown in FIG. 2, sweat patch component 102 includes a sweat biochemical sensor patch 300. FIG. 3 is a schematic view of sweat biochemical sensor patch 300, and FIG. 4 is a perspective view of sweat biochemical sensor patch 300 attached to on-patch electronics module 106. In the exemplary embodiment, sweat biochemical sensor patch 300 may have dimensions of approximately 27 millimeters (mm) by 36.5 mm. Alternatively, sweat biochemical sensor patch 300 may have any dimensions that enable sweat electrolyte sensor patch 300 to function as described herein.

In the exemplary embodiment, sweat biochemical sensor patch 300 includes a plurality of ion selective electrodes (ISEs) 302 for acquiring sweat electrolyte data. Alternatively, or additionally, sweat biochemical sensor patch 300 may include radio frequency (RF) sensors. Further, in other embodiments, sweat biochemical sensor patch 300 may include any biochemical sensor or sensors capable of measuring one or more biochemical parameters (e.g., chemical composition parameters) of sweat.

ISEs 302 include sodium and potassium ISEs in the exemplary embodiment. ISEs 302 (or other biochemical sensors) are printed on a substrate 304, such as polyethylene terephthalate (PET). A side of substrate 304 that faces the skin may be hydrophilic (e.g., having a water contact angle of approximately 20 degrees or less) to allow for full wettability and transport of sweat. As shown in FIGS. 3 and 4, sweat biochemical sensor patch 300 also includes conductive lines 306 for connecting on-patch electronics module 106 to the sweat rate sensor (described in detail below). On-patch electronics module 106 is connected to sweat biochemical sensor patch 300 and the sweat rate sensor through connectors, such as spring contacts 308 (shown in FIG. 4) or a conductive adhesive paste. In some embodiments, a mount ring 310 is used to provide greater mechanical stability during attachment and detachment of on-patch electronics module 106 to sweat biochemical sensor patch 300. In some embodiments, on-patch electronics module 106 (or control module 108) may include individual high-impedance amplifier circuits for electrolytes measured using ISEs 302 (or other biochemical sensors. Further, on-patch electronics module 106 (or control module 108) may include high-impedance amplification circuitry and a multiplexing digital-to-analog converter (DAC), allowing for switching between inputs on a time-defined basis. This enables sending high quality data from multiple sources over a single cable (e.g., cable 110).

Figure 5:
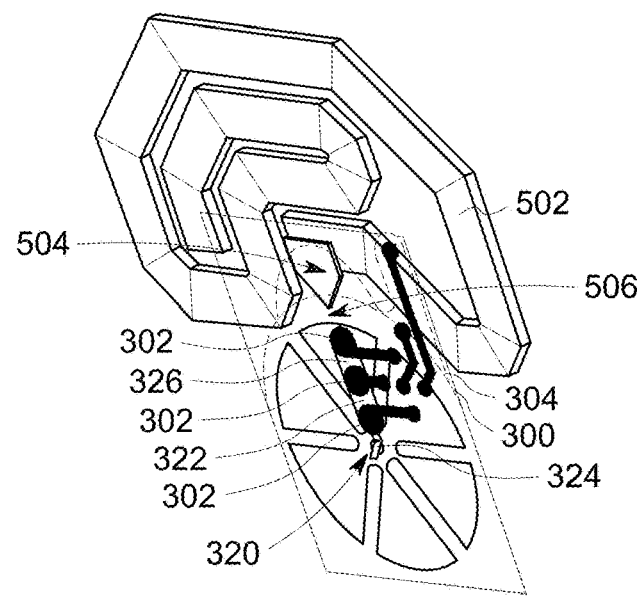
FIG. 5 is a perspective view of an exemplary sweat patch component that may be used with the wearable sweat sensing device shown in FIGS. 1 and 2.

To collect sweat from the user's skin and transport the collected sweat across ISEs 302, sweat biochemical sensor patch 300 includes a number of features. For example, substrate 304 being hydrophilic facilitates collecting sweat. Further, as shown in FIG. 5, a hole 320 is defined through substrate 304, and a capture wick 322 extends across ISEs 302 (or alternatively, other biochemical sensors) and through hole 320. Capture wick 322 is a highly absorbent material that transfers sweat across ISEs 302 (or other biochemical sensors). Specifically, capture wick 322 includes a tip 324 extending through hole 320 and a body 326 coupled to tip 324 and extending across ISEs 302 (or other biochemical sensors). Sweat is captured and collected at tip 324 and flows through body 326 across ISEs 302 (or other biochemical sensors).

As shown in FIG. 5 sweat patch component 102 further includes a wick 502. Wick 502 facilitates measuring sweat rate, as described herein. In the exemplary embodiment, sweat patch component 102 includes a pre-wick 504 that extends towards capture wick 322. Pre-wick 504 may be coupled to wick 502 in some embodiments or be integral with wick 502 in other embodiments such that pre-wick 504 forms part of wick 502. In the exemplary embodiment a gap 506 exists between capture wick 322 and wick 502. Gap 506 facilitates ensuring that capture wick 322 is completely wetted by sweat before sweat is channeled to wick 502. Wick 502 is downstream from capture wick 322. That is sweat flows, in series, through capture wick 322, across gap 506, and through wick 502.

Figure 6:
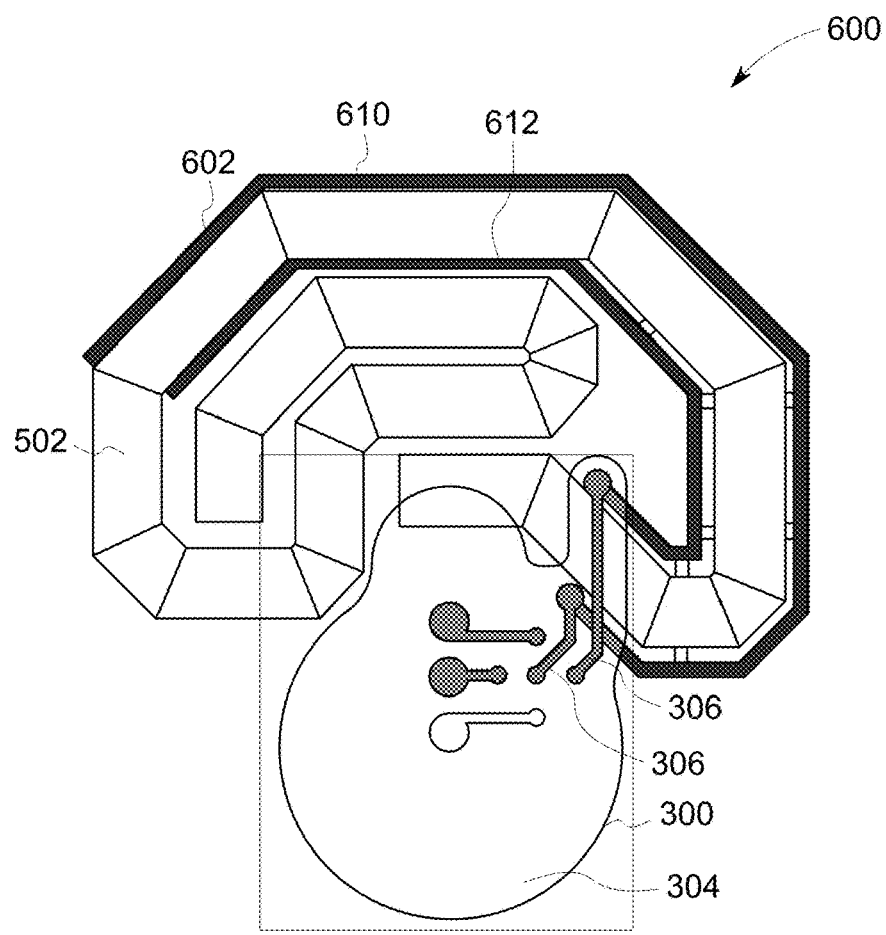
FIG. 6 is a plan view of an exemplary sweat rate sensor that may be used with the wearable sweat sensing device shown in FIGS. 1 and 2.

FIG. 6 is a plan view of a sweat rate sensor 600 of sweat patch component 102. As shown in FIG. 6, wick 502 forms part of a sweat rate sensor of sweat patch component 102. Several different approaches may be used to estimate a sweat rate. In the embodiments described herein, electronic circuitry 602 is printed on a flexible substrate, and subsequently laminated to wick 502. As shown in FIG. 6, in the exemplary embodiment, electronic circuitry 602 includes a first conductive trace 610 and a second conductive trace 612. First and second conductive traces 610 and 612 are each connected (e.g., using conductive adhesives) to an associated conductive line 306 on sweat biochemical sensor patch 300. As sweat is transported through wick 502, the electrical response of electronic circuitry 602 is gradually changed. The mechanism and the magnitude of this change depend on the specific circuitry used, as well as the sweat volume absorbed by the patch. Several examples of sweat rate sensors with the specific circuitry will now be described.

In a first example, the progress of sweat in wick 502 is used to trigger changes in a circuit including well-controlled electronic elements (e.g., resistors and capacitors) that can be sensed easily by low fidelity electronics with only two input/output lines (i.e., first and second conductive traces 610 and 612). When sweat comes into contact with either a conductor or resistor printed on or from a highly water sensitive material, the portion of the circuit crossing the wick dissolves (i.e., becomes disconnected). Using this principle, a ladder circuit can be design such that step-wise changes in resistance due to sweat flow (e.g., in the kilo-Ohm range) can be easily sensed.

Figure 7:
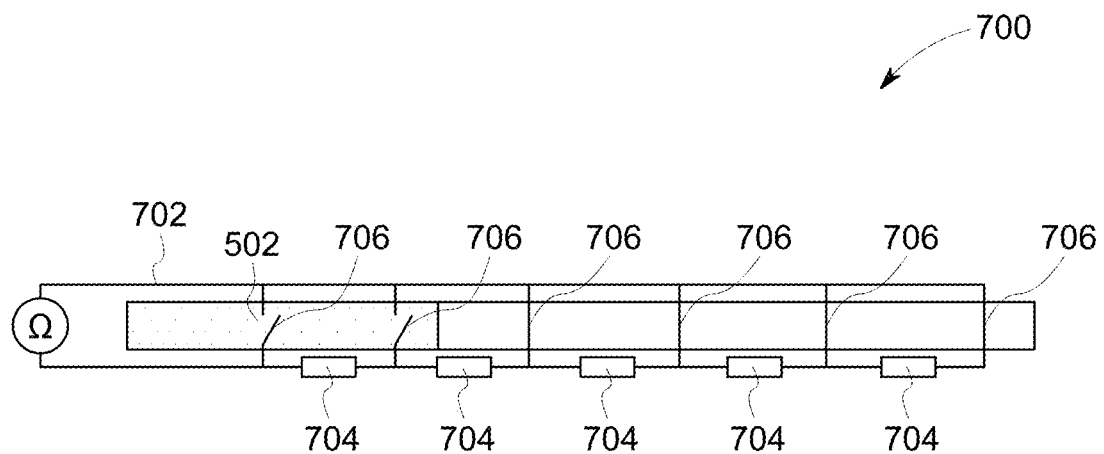
FIG. 7 is a schematic diagram of an exemplary wick structure that may be used with the sweat rate sensor shown in FIG. 6.
Figure 8:
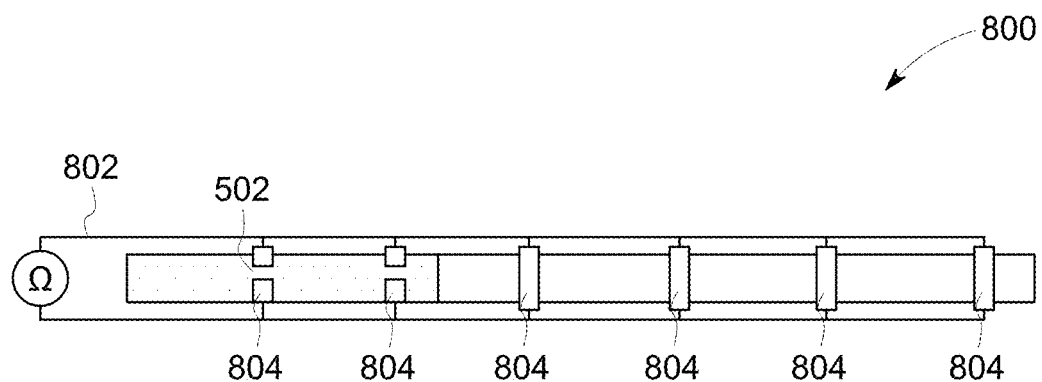
FIG. 8 is a schematic diagram of another exemplary wick structure that may be used with the sweat rate sensor shown in FIG. 6.

FIG. 7 is a schematic diagram of a first wick structure 700 and FIG. 8 is a schematic diagram of a second wick structure 800 that both implement this principle. First wick structure 700 has a circuit 702 include a plurality of resistors 704 and a plurality of breakable links 706 extending across wick 502. As sweat advances through wick 502 (from left to right), links 706 are broken, changing the electrical properties of circuit 702. In one embodiment, resistors 704 have a resistance of approximately 5 kilo-Ohms, and links 706 have a closed resistance of 65 Ohms and an open (i.e., broken) resistance of 650 kilo-Ohms. Accordingly, breaking a last link 706 will result in a large resistance jump (unless the number of links 706 is sufficiently high). This resistance jump may be used, for example, to indicate the end of the test (as sweat has traveled fully through wick 502). In general, resistors 704 should have a higher resistance than the closed resistance of links 706.

Second wick structure 800 includes a circuit 802 having a plurality of water-soluble resistors 804 that extend across wick 502. As sweat advances through wick 502 (from left to right), water-soluble resistors 804 are broken, changing the electrical properties of circuit 802.

To implement first wick structure 700 and second wick structure 800, a conductive (or resistive) trace may be printed on a substrate that is water soluble (e.g., salt, sugar, hydrogel, amorphous organic salt, soluble polymer, etc.) or water swellable (e.g., toilet tissue, spy paper, polymer gel, etc.). Upon water exposure, the substrate will either dissolve away or swell to such a point that the conductive (or resistive) trace is disconnected. Alternatively, a conductive (or resistive) trace from a water soluble or water swellable ink formulation (e.g., carbon black with sugar, salt, or starch binder, metallic particles in a highly swellable hydrogel, etc.) can be printed onto a non-reactive substrate. In this case, upon water exposure, the conductive (or resistive) trace will either totally dissolve in water or its electrical properties will be significantly altered.

The printed circuitry elements described above may be implemented in sweat rate sensor 600 (shown in FIG. 6). In the exemplary embodiment, the combination of wick 502 and electronic circuitry 602 may be printed in layers. For example, a first layer of swellable hydrogel may be printed using cellulose, pullulan, gelatin, sodium alginate, pectin, rosin, starch, and/or chitosan, which are film forming materials that dissolve rapidly (e.g., within a few minutes) when exposed to water or body fluids. Subsequently, a second layer of conductors, and a third layer of resistors may be printed. Finally, a fourth layer of insulator (i.e., forming the fluid-transporting material of wick 502) may be printed.

As another example, in some embodiments, to form the combination of wick 502 and electronic circuitry 602, water soluble conductive carbon-based traces are printed across water resistant conductive traces, and a printed thermoplastic-based urethane is laminated to absorbent wick paper. Subsequently, a phosphate-buffered saline (PBS) solution or salt solution of phone pH and volume is flowed across the paper wick over a controlled period of time. In such embodiments, the sweat rate can be measured based on the resistance as a function of PBS or salt solution volume. In addition to the specific examples given above, those of skill in the art will appreciate that other suitable manufacturing methods may be used to form the combination of wick 502 and electronic circuitry 602.

For instance, in one example, changes in the resistance of printed electrodes laminated to absorbent wick 502 can be used to monitor sweat rate. To validate this, a carbon-based printed resistor printed on thermoplastic polyurethane (TPU) was laminated to a GF/D paper strip and then covered with a Tegaderm film. Changes in the overall resistance in the direction of flow (due to changes in resistance of the wick during salt/water absorption) were then measured with a voltmeter during continuous addition of PBS.

In another example, the absorbent wick may be modified such that salt, ion-absorbing, or particle array bridges are incorporated into wick 502. In this example, upon sweat flow, instead of a gradual change in the resistance, a step change in the resistance may occur.

In other examples, sweat rate may be monitored using capacitance changes. For example, a capacitor may be fabricated from two conducting films and a wick positioned between the two conducting films. The capacitance is determined by the spacing between the two capacitor plates (the two conducting films), and the dielectric material (the wick) which can absorb sweat. Sweat flowing through the wick causes changes in the capacitance, and a linear relationship between salt solution volume (i.e., sweat) and capacitance may be observed. In yet other examples, sweat rate may be monitored based on conductivity using simple electrodes positioned in the direction of sweat wicking.

In some embodiments, wick 502 (and thus the sweat rate sensor) may not be adhered to the body, but may remain part of a disposable sweat patch. Not including adhesive from the skin-contacting area of the patch and allowing it to instead float freely results in at least some advantages. For example, in such embodiments, a capacitive sensor (such as that described above) will not experience mechanical deformations due to bodily motions/flextures/extensions. Further, the user would not feel the presence of a rigid sensor attached to their skin (as the sensor will not bend, flex, or stretch with the skin. Finally, an occluded skin area would be minimized, decreasing hydromeiotic effects.

Figure 9:
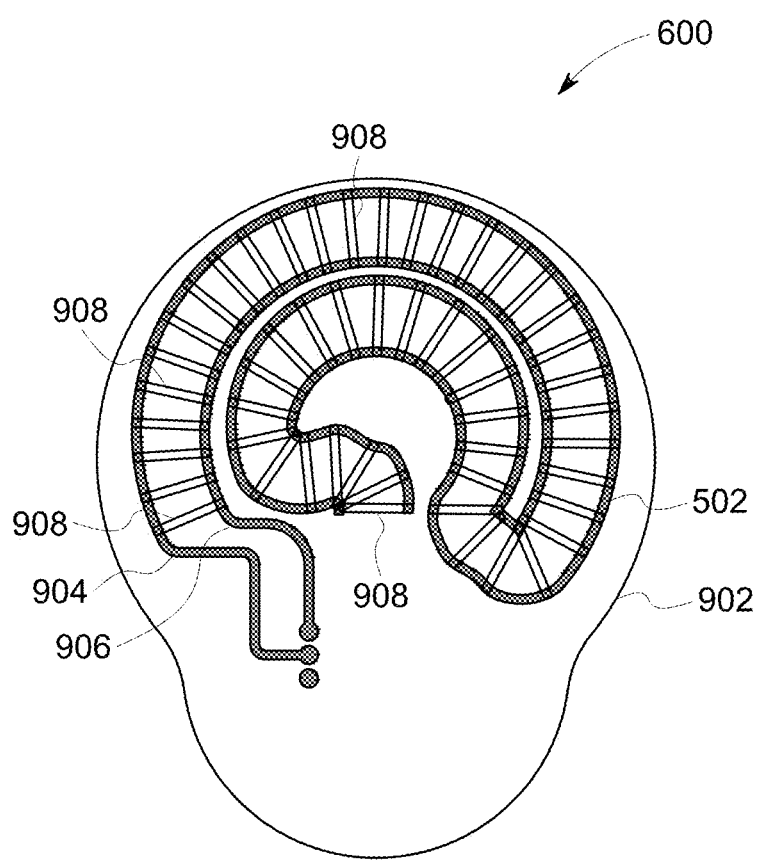
FIG. 9 is a schematic diagram of one embodiment of a sweat rate sensor.

FIG. 9 is a schematic diagram of one embodiment of sweat rate sensor 600. In the embodiment shown in FIG. 9, sweat rate sensor 600 includes wick 502 positioned on a sweat rate sensor layer 902. As shown in FIG. 9, wick 502 includes a first conductor 904, a second conductor 906, and a plurality of dissolvable resistors 908 extending between first and second conductors 904 and 906. As described above in association with FIGS. 6-8, as sweat flows through wick 502 and contacts resistors 908, those resistors 908 will dissolve/breakdown, altering the electrical properties of wick 502, which can be easily sensed using first and second conductors 904 and 906. This enables monitoring the rate that sweat flows through wick 502.

Figure 10:
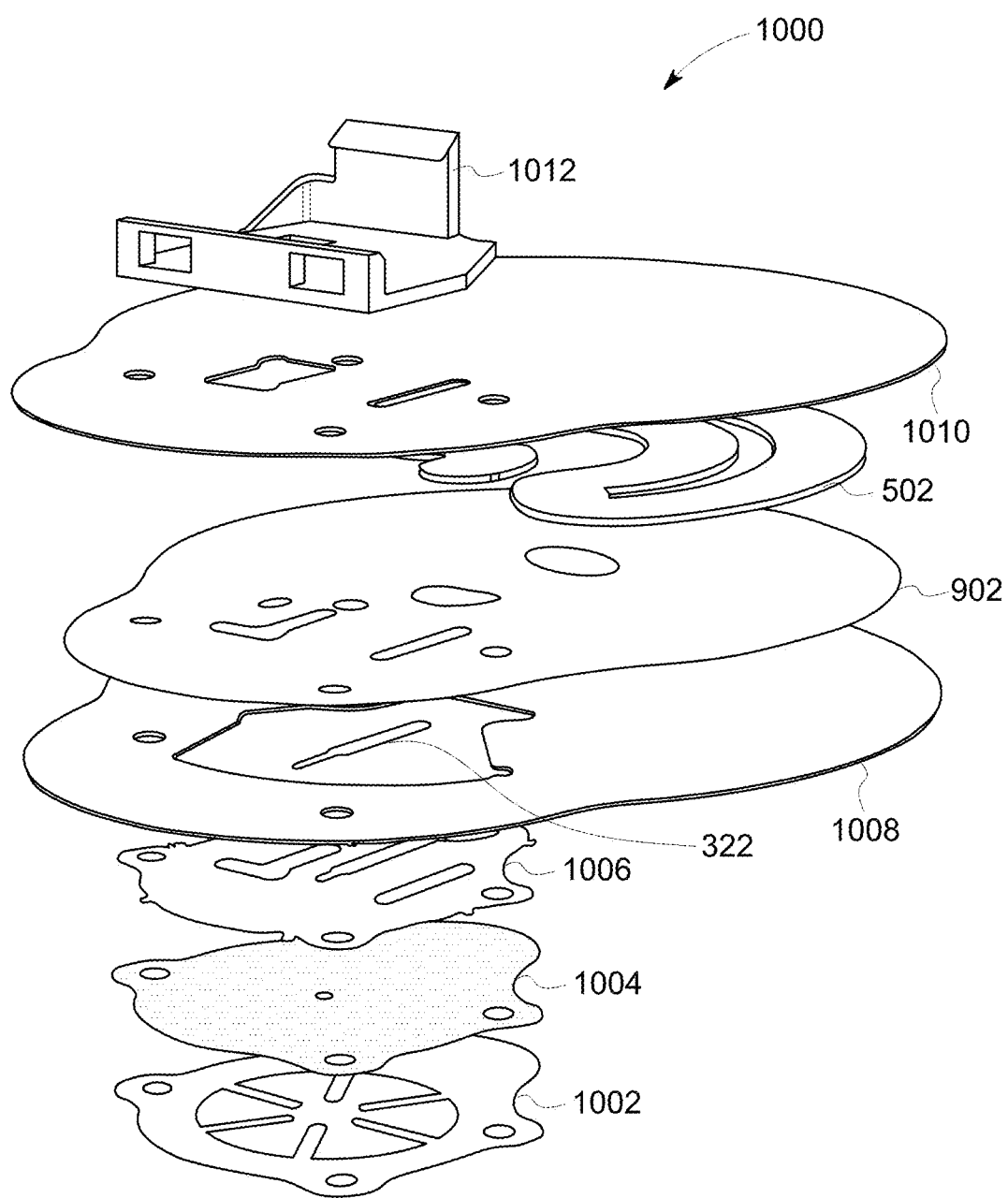
FIG. 10 is an exploded view of an exemplary sweat sensor assembly.

FIG. 10 is an exploded view of an exemplary sweat sensor assembly 1000 that may be used to implemented sweat patch component 102. Sweat sensor assembly 1000 includes a series of layers. In the exemplary embodiment, sweat sensor assembly 1000 includes a sweat collection area adhesive 1002 that contacts and adheres to the wearer's skin and defines the boundaries of the sweat collection area, a printed electrolyte sensor layer 1004 (e.g., including ISEs 302), a fluidic layer 1006, and a skin adhesion layer 1008 that also contacts and adheres to the wearer's skin. The skin adhesion layer 1008 defines horizontal boundaries of the fluid path, and a non-porous layer may be used to confine the fluid flow vertically. Before adhering sweat sensor assembly 1000 to the wearer's skin, the skin may be prepared by removing excess hair, dead skin, and/or excess oils.

In the exploded view of FIG. 10, capture wick 322 is shown positioned within an aperture of skin adhesion layer 1008. Further, sweat sensor assembly 1000 includes sweat rate sensor layer 902, wick 502, and a top layer 1010. A mount plate 1012 is sized to receive on-patch electronics module 106 (not shown in FIG. 10) to physically couple on-patch electronics module 106 to sweat sensor assembly 1000. Those of skill in the art will appreciate that sweat sensor assembly 1000 shown in FIG. 10 is an exemplary embodiment, and that other embodiments of sweat sensor assemblies within the scope of this disclosure may include different configurations, types, numbers, and/or orientation of layers.

Turning now to electronics module component 104, as described above, on-patch electronics module 106 and control module 108 are connected via cable 110. Cable 110 may be, for example, a headphone audio extension cord or the like. In the exemplary embodiment, on-patch electronics module 106 includes amplifiers (e.g., for amplifying signals from ISEs 302), voltage reference circuits, and an analog-to-digital converter (ADC)/multiplexer (MUX). Accordingly, on-patch electronics module 106 converts measurements from analog to digital signals before transmitting those signals to control module 108 in the exemplary embodiment. Alternatively, on-patch electronics module 106 may include any circuitry that enables on-patch electronics module 106 to function as described herein. On-patch electronics module 106 has a small footprint, and is low-weight and low-profile, improving device comfort and wearability, and improving mechanical and electrical reliability of the device during natural body movements because internal mechanical stresses are significantly reduced.

Further, in the exemplary embodiment, control module 108 includes a memory device and a microcontroller (MCU). Control module 108 may also include a wireless communications unit (e.g., a Bluetooth unit), power management circuitry, and a battery unit. The battery unit may be rechargeable, for example, using induction charging. The battery unit may, for example, power the device for up to six hours during high exertion/sweat rate conditions. In some embodiments, the battery unit (or other components of wearable sweat sensing device 100) may be powered by sweat (e.g., using salt-based batteries). Further, in some embodiments, to reduce power consumption, one or more components of wearable sweat sensing device 100 may remain inactive until the presence of sweat is detected. In some embodiments, memory device may be a microSD card or other data storage device that is removably insertable into or permanently installed in control module 108.

Control module 108 is capable of wireless communication with remote computing device (e.g., a mobile computing device) using Bluetooth communications or alternative approaches such as direct Wi-Fi. Further, control module 108 is capable of bi-directional communication, allowing control module 108 or the remote computing device to store and recall prior data in the event of a communications breakdown.

In some embodiments, control module 108 communicates with an associated software application installed on a mobile computing device. The software application may include multiple functions that assist a user in using wearable sweat sensing device 100. For example, the software application may assist a user in identifying sweat patch component 102 and entering calibration data (e.g., calibration data for ISEs 302 for conversion of the incoming data to electrolyte concentrations and sweat volume). The software application may also upload all data to a cloud storage system, include algorithms for analyzing trends in the data, and enable users to customize the data analysis. The software application may also enable data (in a raw form or subsequent to analysis and conversion into a relevant physiological hydration index) to be displayed on the mobile computing device. For example, in some embodiments, the software application (or control module 108 itself) may calculate a hydration index based on first measurements from a sweat biochemical sensor, and second measurements from a sweat rate sensor, as described herein. Further, the software application may generate an alarm when hydration levels deviate from an expected range. Further, data may be stored on control module 108 as a backup, and downloaded to mobile communications device upon re-establishment of communications.

Figure 11:
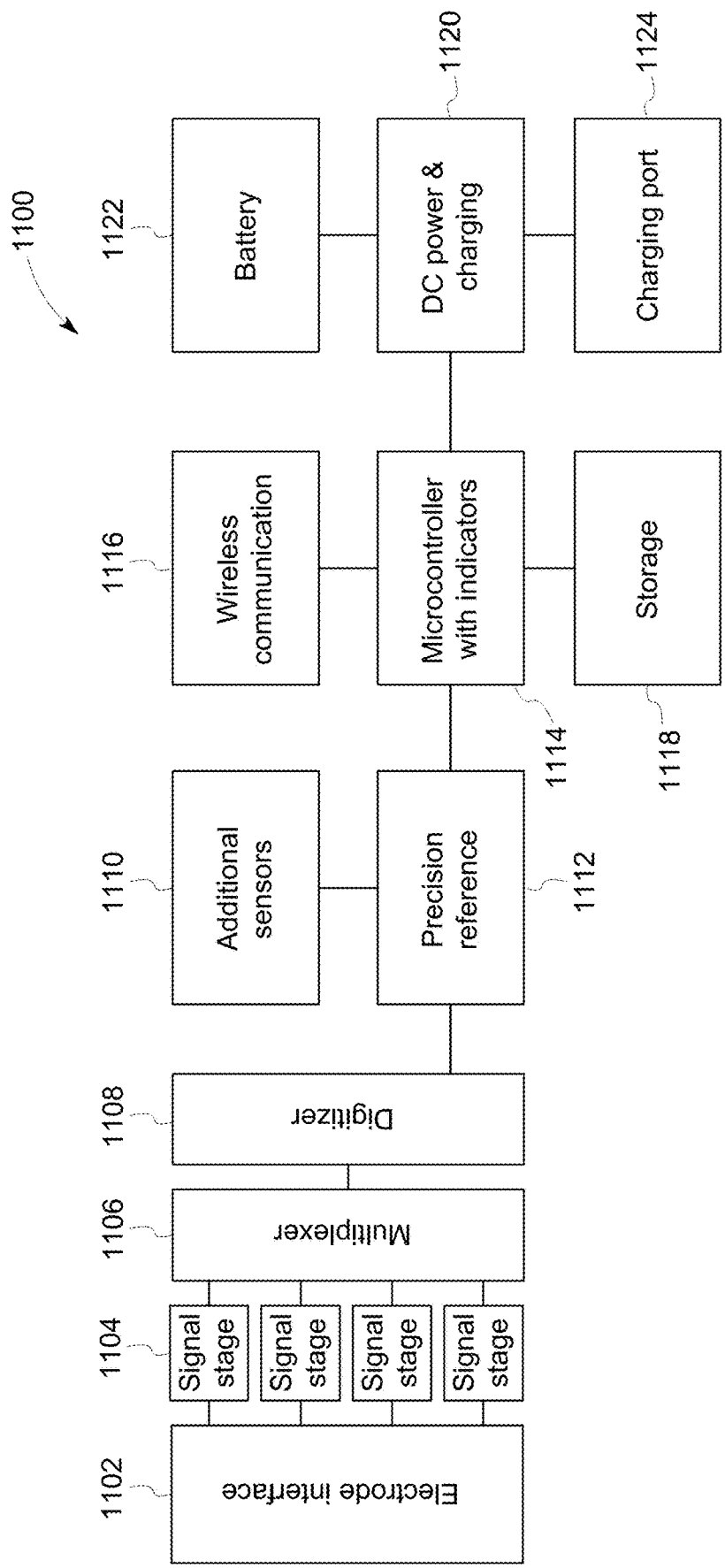
FIG. 11 is a block diagram of an exemplary electronics architecture.

FIG. 11 is a block diagram of an exemplary electronics architecture 1100. Components within electronics architecture 1100 may be included within on-patch electronics module 106 and/or control module 108. In the exemplary embodiment, electronics architecture 1100 includes an electrode interface 1102 (e.g., for interfacing electronics architecture 1100 to sensing electrodes on sweat patch component 102, such as ISEs 302, first and second conductors 904 and 906, etc.). Electrode interface 1102 supplies signals through a plurality of signal stages 1104 to a multiplexer 1106 and a digitizer 1108. Digitizer 1108 and any additional sensors 1110 are coupled to precision reference circuitry 1112, which is in turn coupled to a microcontroller 1114 (i.e., a processing device).

Microcontroller 1114 is coupled to a wireless communication device 1116 to enable wireless communications for electronics architecture 1100. Further, microcontroller 1114 is coupled to a storage device 1118, which may be a removable or non-removable memory device. In the exemplary embodiment, microcontroller 114 is further coupled to a direct current (DC) power and charging module 1120, which is in turn coupled to a battery 1122 and a charging port 1124. Those of skill in the art will appreciate that electronics architecture 1100 may include less, additional, and/or different components than those shown in FIG. 11.

The embodiments described herein include systems and methods for wearable sweat sensing devices. A wearable sweat sensing device includes a sweat patch component including a sweat biochemical sensor patch having a substrate defining a hole therethrough, at least one biochemical sensor printed on the substrate, and a capture wick extending across the at least one biochemical sensor. The capture wick includes a tip that extends through the hole defined through the substrate to reach the skin of a wearer, and the capture wick is configured to channel sweat from the skin of the wearer across the at least one biochemical sensor. The sweat patch component further includes a wick downstream from the capture wick and separated from the capture wick by a gap. The wick is configured to channel sweat received via the capture wick. Further, electronic circuitry is disposed against at least one face of the wick, and an electronic response of the electronic circuitry changes as sweat flows through the wick. An electronics module component is communicatively coupled to the sweat patch component, and is configured to facilitate assessing hydration of a wearer based on signals from the at least one biochemical sensor and the electronic circuitry.

An exemplary technical effect of the methods, systems, and apparatus described herein includes at least one of: (a) reducing a footprint, profile, and weight of sweat sensing systems; (b) providing both sweat rate sensing and sweat biochemical sensing in the same device; and (c) wirelessly communicating sweat sensing data to a remote computing device for storage and analysis.

Exemplary embodiments for wearable sweat sensing devices are described herein. The systems and methods are not limited to the specific embodiments described herein, but rather, components of systems and/or steps of the methods may be utilized independently and separately from other components and/or steps described herein. For example, the methods may also be used in combination with other systems, and are not limited to practice with only the systems described herein. Rather, the exemplary embodiment can be implemented and utilized in connection with many other systems.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A wearable sweat sensing device comprising:
a sweat patch component comprising:
a sweat biochemical sensor patch comprising:
a substrate defining a hole therethrough;
at least one biochemical sensor printed on said substrate; and
a capture wick extending across said at least one biochemical sensor and including a tip that extends through the hole defined through said substrate to reach the skin of a wearer, said capture wick configured to channel sweat from the skin of the wearer across said at least one biochemical sensor;
a wick downstream from said capture wick and separated from said capture wick by a gap, said wick configured to channel sweat received via said capture wick; and
electronic circuitry comprising first and second conductive traces disposed against at least one face of said wick, wherein an electronic response of said electronic circuitry changes as sweat flows through said wick; and
an electronics module component comprising a processor communicatively coupled to said sweat patch component, said processor configured to facilitate assessing hydration of a wearer based on signals from said at least one biochemical sensor and said electronic circuitry.

2. A wearable sweat sensing device in accordance with claim 1, wherein the gap facilitates ensuring said capture wick is completely wetted by sweat before sweat is channeled to said wick.

3. A wearable sweat sensing device in accordance with claim 1, wherein the electronic response of said electronic circuitry to the presence of sweat is measurable as a change in at least one of resistance, potential, and capacitance.

4. A wearable sweat sensing device in accordance with claim 1, wherein said electronic circuitry comprises a plurality of water-soluble resistors extending between the first and second conductive traces.

5. A wearable sweat sensing device in accordance with claim 1, wherein said electronics module component comprises individual high-impedance amplifier circuits for electrolytes measured using said at least one biochemical sensor.

6. A wearable sweat sensing device in accordance with claim 1, wherein said electronics module component comprises high-impedance amplification circuitry and a multiplexing digital-to-analog converter (DAC), allowing for switching between inputs on a time-defined basis.

7. A wearable sweat sensing device in accordance with claim 1, wherein said substrate comprises a hydrophilic, non-porous material.

8. A wearable sweat sensing device in accordance with claim 1, wherein said electronics module component is reusable, and wherein said sweat patch component is disposable.

9. A wearable sweat sensing device in accordance with claim 1, wherein said electronics module component comprises:
   an analog-to-digital signal module component coupled to said sweat patch component, said analog-to-digital signal module component comprising at least one amplifier for amplifying a signal measured by said at least one biochemical sensor; and
   a control module communicatively coupled to said analog-to-digital signal module component.

10. A wearable sweat sensing device in accordance with claim 9, wherein said analog-to-digital signal module is communicatively coupled to said control module using a cable.

11. A wearable sweat sensing device in accordance with claim 9, wherein said analog-to-digital signal module is in wireless communication with said control module.

12. A wearable sweat sensing device in accordance with claim 9, wherein said control module comprises a wireless communication unit in communication with said processor and configured to wirelessly communicate with a mobile computing device.

13. A method of assessing hydration of a subject, the method comprising:
   adhering a sweat patch component to the subject, the sweat patch component including a capture wick that extends across at least one biochemical sensor, a wick downstream from the capture wick and separated from the capture wick by a gap, and electronic circuitry including first and second conductive traces disposed against at least one face of the wick;
   receiving signals from the at least one biochemical sensor and the electronic circuitry as sweat is channeled through the capture wick and the wick, wherein an electronic response of the electronic circuitry changes as sweat flows through the wick; and
   assessing hydration of the subject based on the signals received from the at least one biochemical sensor and the electronic circuitry.

14. A method in accordance with claim 13, wherein receiving signals comprises:
   receiving signals at an analog-to-digital signal module component;
   converting the received signals into digital signals; and
   transmitting the digital signals to a control module.

15. A method in accordance with claim 14, wherein transmitting the digital signals comprises transmitting the digital signals over a cable coupling the analog-to-digital signal module component to the control module.

16. A method in accordance with claim 14, wherein transmitting the digital signals comprises wirelessly transmitting from the analog-to-digital signal module component to the control module.

17. A sweat patch component for a wearable sweat sensing device, said sweat patch component comprising:
   a sweat biochemical sensor patch comprising:
      a substrate defining a hole therethrough;
      at least one biochemical sensor printed on said substrate; and
      a capture wick extending across said at least one biochemical sensor and including a tip that extends through the hole defined through said substrate to reach the skin of a wearer, said capture wick configured to channel sweat from the skin of the wearer across said at least one biochemical sensor;
      a wick downstream from said capture wick and separated from said capture wick by a gap, said wick configured to channel sweat received via said capture wick; and
      electronic circuitry disposed against at least one face of said wick, said electronic circuitry comprising first and second conductive traces, and a plurality of water-soluble resistors extending between said first and second conductive traces.

18. A sweat patch component in accordance with claim 17, wherein said at least one biochemical sensor comprises an ion-selective electrode.

19. A sweat patch component in accordance with claim 17, wherein the gap facilitates ensuring said capture wick is completely wetted by sweat before sweat is channeled to said wick.

20. A sweat patch component in accordance with claim 17, wherein said sweat patch component has a multi-layer structure.

* * * * *